(12) United States Patent
Panayi et al.

(10) Patent No.: US 8,865,625 B2
(45) Date of Patent: Oct. 21, 2014

(54) HERBICIDAL PICOLINIC ACID SALT COMPOSITION

(75) Inventors: Aristos Panayi, Taylors Hill (AU); Chad Richard Ord Sayer, Brighton (AU)

(73) Assignee: Nufarm Australia Limited, Laverton North (AU)

( * ) Notice: Subject to any disclaimer, the term of this patent is extended or adjusted under 35 U.S.C. 154(b) by 0 days.

(21) Appl. No.: 13/703,509

(22) PCT Filed: Jun. 17, 2011

(86) PCT No.: PCT/AU2011/000730
§ 371 (c)(1),
(2), (4) Date: Mar. 1, 2013

(87) PCT Pub. No.: WO2011/160162
PCT Pub. Date: Dec. 29, 2011

(65) Prior Publication Data
US 2013/0157862 A1  Jun. 20, 2013

Related U.S. Application Data

(60) Provisional application No. 61/356,911, filed on Jun. 21, 2010.

(51) Int. Cl.
*A01N 43/40* (2006.01)
(52) U.S. Cl.
CPC ..................... *A01N 43/40* (2013.01)
USPC ......................... 504/260; 504/130

(58) Field of Classification Search
USPC .......................... 504/130, 244, 260
See application file for complete search history.

(56) References Cited

U.S. PATENT DOCUMENTS

| | | | | |
|---|---|---|---|---|
| 3,317,549 A | * | 5/1967 | Johnston | 546/286 |
| 6,200,929 B1 | * | 3/2001 | Horibe et al. | 504/127 |
| 2010/0331188 A1 | | 12/2010 | Sayer et al. | |
| 2011/0230349 A1 | * | 9/2011 | Buttimor | 504/244 |
| 2012/0058897 A1 | | 3/2012 | Sayer et al. | |

FOREIGN PATENT DOCUMENTS

GB  851084  10/1960
GB  11339315  12/1973

* cited by examiner

*Primary Examiner* — John Pak

(57) ABSTRACT

A herbicidal concentrate composition comprising a mixture of the monomethylamine and dimethylamine salts of at least one picolinic acid herbicide of formula (Ia): wherein $X^2$ is selected from hydrogen and amino.

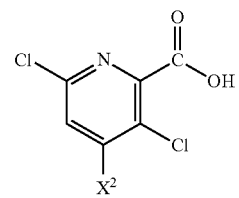

(Ia)

11 Claims, No Drawings

HERBICIDAL PICOLINIC ACID SALT COMPOSITION

FIELD

The invention relates to a herbicidal composition of picolinic acid salts and in particular a composition of monomethylamine and dimethylamine salts of at least one picolinic acid of formula

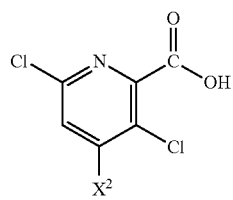

wherein $X^2$ is hydrogen or amino.

BACKGROUND

The picolinic acid class of herbicides comprise a substituted 2-pyridine carboxylic acid group and their ester and salt derivatives. The picolinic acid group of herbicides is used in control of perennial broad leaf weeds by pre emergent application to soil and post emergent foliar or soil application. They are useful in control of broadleaf weeds in grasses.

Examples of picolinic herbicidal compounds include compounds of formula (I)

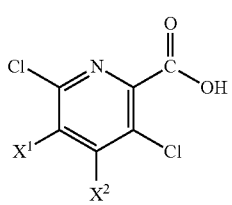

wherein
$X^1$ and $X^2$ are independently selected from hydrogen, chloro and amino; and
R is an ester or salt counter ion.

Specific examples of known picolinic acid herbicides include aminopyralid (4-amino-3,6-dichloropyridine-2-carboxylic acid) its esters and salts, picloram (4-amino-3,5,6-trichloropyridine-2-carboxylic acid also referred to as 4-amino-3,4,6-trichloropicolinic acid) its salts and esters and clopyralid (3,6-dichloropyridine-2-carboxylic acid also called 3,6-dichloropicolinic acid) its salts and esters.

The amine salts of the picolinic acid herbicides are in many cases water soluble and aqueous formulations of the amine salts are convenient to use. At the site of use the concentrate formulations can conveniently be diluted in a spray tank for soil or foliar application.

One of the significant limitations of amine salt compositions is their stability, particularly at high loadings. The poor solution stability is particularly a problem for low temperature storage of highly concentrated solutions, for example of at least 300 g/L and particularly at least 500 g/L (based on active acid equivalent). This places limitations on the storage and handling of the herbicidal picolinic acid amine salts with the result that the loading of salt needs to be lower than would normally be stable due to the propensity to form a significant proportion of crystalline deposits at low temperature which are not always readily redissolved.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

We have found that the stability of certain picolinic acids in aqueous solution may be significantly improved allowing significantly higher loadings to be used by using a mixture of the monomethyl amine (MMA) and dimethylamine (DMA) salts of one or more picolinic acids.

Accordingly there is provided a herbicidal concentrate composition comprising a mixture of the monomethylamine and dimethylamine salts of at least one picolinic acid herbicide of formula (Ia)

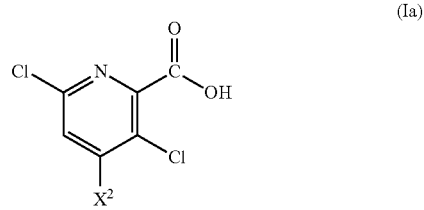

wherein $X^2$ is hydrogen or amino;

The mole ratio of monomethylamine to dimethylamine is, in one set of embodiments, in the range of from 5:95 to 95:5, preferably 10:90 to 90:10 and more preferably 20:80 to 80:20. In one set of embodiments the particularly preferred ratio is in the range of 70%-90% DMA to 30%-10% MMA. We found that this enhancement was not observed for picloram and was especially advantageous for clopyralid.

The picolinic acid component of the salts may be selected from the group consisting of aminopyralid and clopyralid and mixtures thereof.

The picolinic acid herbicide is preferably clopyralid, aminopyralid or mixture thereof.

The composition may comprise aminopyralid, clopyralid or mixture thereof in the form of one of the MMA salt and aminopyralid, clopyralid or mixture thereof in the form of the DMA salt. The composition in each form may be the same or different. In one set of embodiments the composition comprises clopyralid in each of the MMA and DMA salt forms. The picolinic acid may be aminopyralid or clopyralid and clopyralid is more preferred.

In an embodiment the concentration of picolinic acid herbicide of formula (Ia) in the form of the salts in the aqueous composition is at least 300 g/L (preferably at least 400 g/L, more preferably at least 500 g/L, more preferably at least 600 g/L still more preferably at least 625 g/L, still more preferably 650 g/L and still more preferably at least 700 g/L) based on herbicidal acid equivalent.

In one embodiment there is provided a solid composition for forming the aqueous liquid herbicide composition on dilution with water the solid composition comprising at least one of clopyralid and aminopyralid comprising a mixture of monomethylamine and dimethylamine salts and wherein the molar ratio of monomethylamine to dimethylamine is preferably from 5:95 to 95:5, more preferably 10:90 to 90:10 and still more preferably 20:80 to 80:20. In one set of embodiments the particularly preferred ratio is in the range of 70%-90% DMA to 30%-10% MMA.

In one embodiment the total MMA and DMA comprises at least 80% and more preferably from 80% to 130% by mole based on the number of mole of clopyralid and aminopyralid.

In another embodiment there is provided a process for preparing a composition described above comprising: providing at least one herbicidal picolinic acid of formula (I) (preferably clopyralid) and reacting the herbicide with methylamine and dimethylamine in a molar ratio of preferably 5:95 to 95:5, more preferably 10:90 to 90:10 and still more preferably 20:80 to 80:20 to provide a mixture of picolinic acid methylamine and dimethylamine salts. In one set of embodiments the particularly preferred ratio is in the range of 70%-90% DMA to 30%-10% MMA.

In another embodiment there is provided a method of preparing an aqueous liquid herbicide composition comprising dissolving monomethylamine salt of at least one of aminopyralid and clopyralid (preferably clopyralid) and dimethylamine salt of at least one of aminopyralid and clopyralid (preferably clopyralid) in an aqueous liquid to provide a composition as herein before described.

In one embodiment the above described concentrate further comprises a mixture comprising one or more other herbicides, including for example one or more herbicides selected from the group consisting of auxin herbicides such as MCPA and 24D; glycine herbicides such as glyphosate; and benzoic acid herbicides such asdicamba.

Throughout the description and the claims of this specification the word "comprise" and variations of the word, such as "comprising" and "comprises" is not intended to exclude other additives, components, integers or steps.

DETAILED DESCRIPTION

The composition comprises a mixture of MMA and DMA salts of at least one of aminopyralid and clopyralid herbicides with, in one set of embodiments, the molar ratio of MMA to DMA being in the range of from 5:95 to 95:5, preferably 10:90 to 90:10 and more preferably 20:80 to 80:20. In one set of embodiments the particularly preferred ratio is in the range of 70%-90% DMA to 30%-10% MMA.

The picolinic acid salt mixture is from a parent acid selected from compounds of formula (Ia)

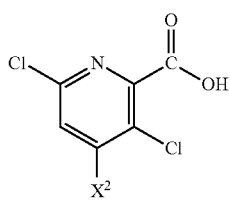

(Ia)

wherein
$X^2$ is selected from hydrogen and amino and mixtures of two or more thereof. Preferably the mixed salts are of clopyralid.

Specific examples of picolinic acid herbicides of formula (Ia) include aminopyralid (4-amino-3,6-dichloropyridine-2-carboxylic acid) and clopyralid (3,6-dichloropyridine-2-carboxylic acid also called 3,6-dichloropicolinic acid) and mixtures of two or more thereof.

While the composition may if desired include other herbicides including other amine salts of picolinic acid or auxin herbicide salts it is preferred that the monomethylamine and dimethylamine constitute at least 80% by weight of the amine content of the composition, preferably at least 90% by weight of the amine content and most preferably at least 95% by weight of the amine content.

Preferably the amine MMA and DMA will be present in a compound concentration in an amount of 80% to 130% by mole based on the total number of marks of clopyralid and aminopyralid.

Preferably the total of clopyralid and aminopyralid will constitute at least 70%, preferably at least 80% and more preferably at least 90% by mole of the total active herbicide content of the composition.

In a particularly preferred embodiment the concentration of herbicidal picolinic acid salt is at least 300 g/L (preferably at least 400 g/L, more preferably at least 500 g/L, more preferably at least 600 g/L, still more preferably 625 g/L, still more preferably 650 g/L and still more preferably at least 700 g/L) based on herbicidal acid equivalent.

The process for preparing the picolinic acid mixed salts may comprise providing at least one of clopyralid and aminopyralid (preferably clopyralid) and reacting the acids with monomethylamine and dimethylamine, preferably in a molar ratio of 5:95 to 95:5, more preferably 10:90 to 90:10 and still more preferably 20:80 to 80:20. In one set of embodiments the particularly preferred ratio is in the range of 70%-90% DMA to 30%-10% MMA, to provide a mixture of methylamine and dimethylamine salts of at least one of clopyralid and amino pyralid (preferably clopyralid).

Alternatively the process may comprise blending the salts, for example blending preformed solids, or dissolving a monomethylamine salt of at least one of aminopyralid and clopyralid and dimethylamine salt of at least one of aminopyralid and clopyralid in an aqueous liquid to provide a composition as hereinbefore described.

In one embodiment there is provided a method of controlling plant growth comprising diluting a concentrate composition comprising at least 300 g/L (preferably at least 400 g/L, more preferably at least 500 g/L, still more preferably at least 600 g/L, still more preferably 625 g/L, still more preferably 650 g/L and still more preferably at least 700 g/L) based on herbicidal acid equivalent of a mixture of MMA and DMA salts of at least one of clopyralid and aminopyralid (preferably clopyralid) with water and applying the diluted composition to plants or to soil in which growth of plants are to be controlled. The composition may, for example, be diluted with water to provide a concentration of clopyralid and aminopyralid (preferably solely clopyralid) herbicide salt in the range of from 0.01 g/L to 300 g/L (based on acid equivalent). The composition may be diluted for spray application to a concentration of 0.1 g/L to 150 g/L of for specific contact application using an applicator such as a rope or wick higher concentration of, for example 50 to 300 g/L may be desired.

The salt concentrate composition may, for example, depending on the picolinic acid salt mixture to be applied at a rate of from 0.01 kg/ha to 5 kg/ha based on total acid equivalent in order to achieve control of weeds.

In some cases solvents may be used in the concentrate picolinic acid salt compositions. Solvents such as ethylene glycol, may be used to further limit the formation of crystalline deposits during storage of the aqueous liquid concentrate. The compositions may, if desired, be free of non-aqueous solvents such as ethylene glycol. Accordingly in one embodiment the herbicide composition comprising a solution of salt of picolinic acid of formula (Ia) in the form of the monomethylamine salt and dimethylamine salt of picolinic acid of formula (Ia) wherein the molar ratio of monomethylamine to dimethylamine is preferably in the range of from 5:95 to 95:5, preferably 10:90 to 90:10 and more preferably 20:80 to 80:20 and may contain no more than 5% by weight non-aqueous solvents and more preferably is essentially free of non-aqueous solvents.

In one set of embodiments the particularly preferred ratio is in the range of 70%-90% DMA to 30%-10% MMA.

In a further embodiment the composition consists essentially of:
i) clopyralid salt herbicide in the form of the monomethylamine salt and clopyralid in the form of the dimethylamine salt wherein the molar ratio of monomethylamine to dimethylamine is preferably in the range of from 5:95 to 95:5, preferably 10:90 to 90:10 and more preferably 20:80 to 80:20. In one set of embodiments the particularly preferred ratio is in the range of 70%-90% DMA to 30%-10% MMA.
ii) water;
iii) no more than 10% by weight, preferably no more than 5% and more preferably no more than 2% by weight based on the total weight of the composition of additives selected from surfactants and compatibility agents; and
iv) wherein the concentration of clopyralid salt herbicide in the aqueous composition is at least 300 g/L (preferably at least 400 g/L, more preferably at least 500 g/L, more preferably 600 g/L, more preferably at least 625 g/L, still more preferably 650 g/L and still more preferably at least 700 g/L) based on acid herbicidal acid equivalent.

The composition of the invention may and preferably will include a sequestriant/compatibility agent such as casein or EDTA which we have found to improve compatibility of the salts of picolinic acid of formula (Ia) and other herbicides. The amount of compatibility agent may be at least a compatibility enhancing amount. In a preferred embodiment the composition according to the invention further comprising casein in an amount of from 0.05 to 10 parts by weight casein per 100 parts by weight acid equivalent based on the picolinic acid of formula (Ia). The amount of casein is preferably from 0.01 to 5% by weight of a concentrate composition and more preferably is from 0.1 to 5% by weight of the composition.

The concentrate composition and or composition diluted with water may comprise one or more surfactants. Examples of surfactants include, nonaromatic-based surfactants, e.g. those based on heterocycles, olefins, aliphatics or cycloaliphatics, for example surface-active mono- or poly-alkyl-substituted and subsequently derivatized, e.g. alkoxylated, sulfated, sulfonated or phosphated, pyridine, pyrimidine, triazine, pyrole, pyrrolidine, furan, thiophene, benzoxazole, benzthiazole and triazole compounds, and/or aromatic-based surfactants, e.g. mono- or poly-alkyl-substituted and subsequently derivatized, e.g. alkoxylated, sulfated, sulfonated or phosphated, benzenes or phenols. The surfactants are generally soluble in the solvent phase and are preferably suitable for emulsifying it (together with active ingredients dissolved therein) upon dilution with water to give a spray liquor. The surfactant component when present in compositions according to the invention can, for example, comprise nonaromatic or aromatic surfactants or mixtures of non-aromatic and aromatic surfactants.

The mixed salt picolinic acid herbicides of formula (Ia) (preferably clopyralid) with the preferred 5:95 to 95:5, preferably 10:90 to 90:10 and more preferably 20:80 to 80:20 molar ratio of MMA:DMA exhibit an enhanced cold storage stability and reduced crystal growth at cold temperatures. The compositions also exhibit an improvement in stability in solution when diluted with water of variable quality that tends to produce precipitation in other picolinic acid salts in concentrate compositions. In one set of embodiments the particularly preferred ratio is in the range of 70%-90% DMA to 30%-10% MMA.

The invention will now be described with reference to the following examples. It is to be understood that the examples are provided by way of illustration of the invention and that they are in no way limiting to the scope of the invention.

EXAMPLES

The following compositions were prepared and the composition stability tested on cold storage.

| Example | Formulation details | | Comments |
|---|---|---|---|
| Comparative Example 1 | 700 g/L Clopyralid (as MMA salt) | | Formulation is not stable. Crystallizes @ Room Temperature. |
| | Clopyralid tech 93% | 736.8 g | |
| | Monomethylamine(MMA) 40% | 287.1 g | |
| | Water to | 1 liter | |
| Comparative Example 2 | 650 g/L Clopyralid (as MMA salt) | | Formulation is not stable. Crystallizes @ Room Temperature. |
| | Clopyralid tech 93% | 684.2 g | |
| | MMA 40% | 266.6 g | |
| | Water to | 1 liter | |
| Comparative Example 3 | 600 g/L Clopyralid (as MMA salt) | | Formulation is not stable. Crystallizes @ Room Temperature. |
| | Clopyralid tech 93% | 631.6 g | |
| | MMA 40% | 246.1 g | |
| | Water to | 1 liter | |
| Comparative Example 4 | 550 g/L Clopyralid (as MMA salt) | | Formulation is not stable. 100% Crystallization after 24 hrs @ 0° C. |
| | Clopyralid tech 93% | 579.0 g | |
| | MMA 40% | 225.6 g | |
| | Water to | 1 liter | |
| Comparative Example 5 | 600 g/L Clopyralid (as TEA salt) | | Clopyralid acid does not solubilize completely. Clopyralid-TEA salt is not soluble at this concentration. |
| | Clopyralid tech 93% | 631.6 g | |
| | TriethylamineTEA85% | 576.0 g | |
| | Water to | 1 liter | |
| Comparative Example 6 | 500 g/L Clopyralid (as TEA salt) | | Clopyralid acid does not solubilize completely. Clopyralid-TEA salt is not soluble at this concentration. |
| | Clopyralid tech 93% | 526.3 g | |
| | TEA 85% | 480.0 g | |
| | Water to | 1 liter | |
| Comparative Example 7 | 400 g/L Clopyralid (as TEA salt) | | ~40% v/v crystallisation after 7 days @ 0° C. with seeding using |
| | Clopyralid tech 93% | 421.1 g | |

-continued

| Example | Formulation details | | Comments |
|---|---|---|---|
| | TEA 85% | 384.0 g | crystals from the formulation. |
| | Water to | 1 liter | |
| Comparative Example 8 | 700 g/L Clopyralid (as DMA salt) | | ~5% v/v crystallisation after 7 days @ 0° C. with seeding using crystals from the formulation. |
| | Clopyralid tech 93% | 736.8 g | |
| | DimethylamineDMA60% | 287.1 g | |
| | Water to | 1 liter | |
| Comparative Example 9 | 350 g/L Clopyralid (as TEA salt) | | ~2% v/v crystallisation after 5 days @ 0° C. with seeding using crystals from the formulation. |
| | Clopyralid tech 93% | 368.4 g | |
| | TEA 85% | 336.0 g | |
| | Water to | 1 liter | |
| Comparative Example 10 | 800 g/L Clopyralid (as DMA salt) | | ~10% v/v crystallisation after 5 days @ 0° C. with seeding using crystals from the formulation. |
| | Clopyralid tech 93% | 842.1 g | |
| | DMA 60% | 328.1 g | |
| | Water to | 1 liter | |
| Comparative Example 11 | 650 g/L Clopyralid (as DMA salt) | | ~15% v/v crystallisation after 2 days @ 0° C. with seeding using crystals from the formulation. |
| | Clopyralid tech 93% | 684.2 g | |
| | DMA 60% | 266.6 g | |
| | Water to | 1 liter | |
| Example 1 | 700 g/L Clopyralid (80% DMA:20% MMA salt) | | No crystallisation @ 0° C. for 7 days with seeding using crystals from formulation. Passes Low Storage Stability (Collaborative International Pesticides Analytical Council - CIPAC MT39.3) |
| | Clopyralid tech 93% | 736.8 g | |
| | DMA 60% | 229.7 g | |
| | MMA 40% | 57.4 g | |
| | Water to | 1 liter | |
| Comparative Example 13 | 550 g/L Clopyralid (as DMA salt) | | ~5% v/v crystallisation after 1 day @ 0° C. with seeding using crystals from the formulation. |
| | Clopyralid tech 93% | 579.0 g | |
| | DMA 60% | 225.6 g | |
| | Water to | 1 liter | |
| Example 2 | 800 g/L Clopyralid (80% DMA:20% MMA salt) | | ~1-2% v/v crystallisation after 24 hrs @ 0° C. without seeding. |
| | Clopyralid tech 93% | 842.1 g | |
| | DMA 60% | 262.5 g | |
| | MMA 40% | 65.6 g | |
| | Water to | 1 liter | |
| Example 3 | 750 g/L Clopyralid (80% DMA:20% MMA salt) | | ~1-2% v/v crystallisation after 7 day @ 0° C. with seeding using crystals from the formulation. |
| | Clopyralid tech 93% | 789.5 g | |
| | DMA 60% | 246.1 g | |
| | MMA 40% | 61.5 g | |
| | Water to | 1 liter | |
| Example 4 | 750 g/L Clopyralid (70% DMA:30% MMA salt) | | ~1% v/v crystallisation after 7 day @ 0° C. with seeding using crystals from the formulation. |
| | Clopyralid tech 93% | 789.5 g | |
| | DMA 60% | 215.3 g | |
| | MMA 40% | 92.3 g | |
| | Water to | 1 liter | |
| Example 5 | 725 g/L Clopyralid (80% DMA:20% MMA salt) | | No crystallisation @ 0° C. for 7 days with seeding using crystals from formulation. Passes Low Storage Stability (CIPAC MT39.3) |
| | Clopyralid tech 93% | 763.1 g | |
| | DMA 60% | 237.9 g | |
| | MMA 40% | 59.5 g | |
| | Water to | 1 liter | |
| Example 6 | 725 g/L Clopyralid (90% DMA:10% MMA salt) | | ~1% v/v crystallisation after 7 day @ 0° C. with seeding using crystals from the formulation. |
| | Clopyralid tech 93% | 763.2 g | |
| | DMA 60% | 267.6 g | |
| | MMA 40% | 29.7 g | |
| | Water to | 1 liter | |
| Example 7 | 725 g/L Clopyralid (70% DMA:30% MMA salt) | | No crystallisation @ 0° C. for 7 days with seeding using crystals from formulation. Passes Low Storage Stability (CIPAC MT39.3) |
| | Clopyralid tech 93% | 763.2 g | |
| | DMA 60% | 208.2 g | |
| | MMA 40% | 89.2 g | |
| | Water to | 1 liter | |

Comparative Examples 14 to 21

These comparative Examples examine the stability of picloram (a picolinic acid not of formula Ia) compositions containing a mixture of DMA and MMA salts.

| Comparative Example No. | Formulation details | Amount (g) | Comments |
|---|---|---|---|
| 14 | 2,4-D 600 g/L + Picloram 150 g/L (90% DMA:10% MMA) | | The formulation is not stable. Approx. 30% crystallization when the formulation if left to stand @ Room temperature |
| | Picloram acid technical (93%) | 161.3 | |
| | 2,4-D acid technical (97%) | 618.6 | |
| | MMA (40%) | 26.3 | |

-continued

| Comparative Example No. | Formulation details | Amount (g) | Comments |
|---|---|---|---|
| | DMA (60%) | 236.4 | (R.T) for 24 hrs. |
| | water | to 1 L | |
| 15 | 2,4-D 600 g/L + Picloram 150 g/L (60% DMA:40% MMA) | | The formulation is not stable. Approx. 10% crystallization when the formulation if left to stand @ R.T for 24 hrs. |
| | Picloram acid technical (93%) | 161.3 | |
| | 2,4-D acid technical (97%) | 618.6 | |
| | MMA (40%) | 105.1 | |
| | DMA (60%) | 157.6 | |
| | water | to 1 L | |
| 16 | 2,4-D 600 g/L + Picloram 150 g/L (100% DMA) | | The actives are not fully soluble. A large amount of active material remains unreacted/undissolved. |
| | Picloram acid technical (93%) | 161.3 | |
| | 2,4-D acid technical (97%) | 618.6 | |
| | DMA (60%) | 262.7 | |
| | water | to 1 L | |
| 17 | 2,4-D 600 g/L + Picloram 150 g/L (70% DMA:30% MMA) | | The formulation is not stable. Approx. 80% crystallisation when the formulation if left to stand @ R.T for 24 hrs. |
| | Picloram acid technical (93%) | 161.3 | |
| | 2,4-D acid technical (97%) | 618.6 | |
| | MMA (40%) | 78.8 | |
| | DMA (60%) | 183.9 | |
| | water | to 1 L | |
| 18 | 2,4-D 600 g/L + Picloram 150 g/L (100% MMA) | | The actives are not fully soluble. A large amount of active material remains unreacted/undissolved. |
| | Picloram acid technical (93%) | 161.3 | |
| | 2,4-D acid technical (97%) | 618.6 | |
| | MMA (40%) | 262.7 | |
| | water | to 1 L | |
| 19 | 2,4-D 600 g/L + Picloram 150 g/L (20% DMA:80% MMA) | | The actives are not fully soluble. A large amount of active material remains unreacted/undissolved. |
| | Picloram acid technical (93%) | 161.3 | |
| | 2,4-D acid technical (97%) | 618.6 | |
| | MMA (40%) | 210.2 | |
| | DMA (60%) | 52.5 | |
| | water | to 1 L | |
| 20 | 2,4-D 600 g/L + Picloram 150 g/L (40% DMA:60% MMA) | | The actives are not fully soluble. A large amount of active material remains unreacted/undissolved. |
| | Picloram acid technical (93%) | 161.3 | |
| | 2,4-D acid technical (97%) | 618.6 | |
| | MMA (40%) | 157.6 | |
| | DMA (60%) | 105.1 | |
| | water | to 1 L | |
| 21 | 2.4-D 600 g/L + Picloram 150 g/L (50% DMA:50% MMA) | | The actives are not fully soluble. A large amount of active material remains unreacted/undissolved. |
| | Picloram acid technical (93%) | 161.3 | |
| | 2,4-D acid technical (97%) | 618.6 | |
| | MMA (40%) | 131.4 | |
| | DMA (60%) | 131.4 | |
| | water | to 1 L | |

The picloram MMA/DMA salts were found to have poor stability in comparison with the corresponding clopyralid salt mixtures.

The invention claimed is:

1. A herbicidal concentrate composition comprising an aqueous solution of dimethylamine (DMA) and monomethylamine (MMA) salts of clopyralid wherein the concentration of clopyralid is at least 500 g/L based on herbicidal acid equivalent and the mole ratio of the salts is 70% to 90% dimethylamine to 30% to 10% monomethylamine.

2. A herbicidal concentrate according to claim 1 wherein the concentration of clopyralid salts is in the range of from 550 g/L to 800 g/L based on herbicidal acid equivalent.

3. A herbicidal composition according to claim 1 wherein the mixture of salts is present in aqueous solution of concentration of at least 700 g/L, based on herbicidal acid equivalent.

4. A composition according to claim 1 wherein the composition comprises casein in an amount of from 0.01 to 5% by weight of the concentrate composition.

5. A process for preparing a herbicidal concentrate composition comprising providing a sufficient amount of clopyralid acid and reacting the clopyralid acid with a sufficient amount of monomethylamine and dimethylamine in an aqueous liquid and in a molar ratio of from 70-90% dimethylamine to 30-10% monomethylamine to provide a herbicidal concentrate composition as defined according to claim 1.

6. A process for preparing a herbicidal concentrate composition comprising dissolving a sufficient amount of clopyralid monomethylamine salt and a sufficient amount of clopyralid dimethylamine salt in an aqueous liquid to provide a herbicidal concentrate composition as defined according to claim 1.

7. A method of controlling plant growth comprising diluting a concentrate composition according to claim 1 with water and applying the diluted composition to plants or to soil in which growth of plants are to be controlled.

8. A method according to claim 7 wherein the composition is diluted with water to provide a concentration of clopyralid salt in the range of from 0.01 g/L to 300 g/L (based on acid equivalent) and applied to the plants or soil.

9. A composition consisting essentially of:
  i) clopyralid in the form of the monomethylamine salt and clopyralid in the form of the dimethylamine salt wherein the molar ratio of dimethylamine to monomethylamine salts is in the range of from 70%-90% DMA to 30%-10% MMA;
ii) water;
iii) no more than 10% by weight based on the total weight of the composition of additives selected from surfactants and compatibility agents; and
iv) wherein the concentration of clopyralid salt in the aqueous composition is at least 500 g/L based on herbicidal acid equivalent.

10. A composition according to claim 9 wherein the concentration of clopyralid salt herbicide is at least 600 g/L, based on herbicidal acid equivalent.

11. A composition according to claim 10 wherein the concentration of clopyralid salt herbicide is at least 700 g/L, based on herbicidal acid equivalent.

* * * * *